(12) United States Patent
Avigan et al.

(10) Patent No.: US 11,026,921 B2
(45) Date of Patent: Jun. 8, 2021

(54) COMPOSITIONS AND METHODS OF TREATING CANCER

(71) Applicants: Dana-Farber Cancer Institute, Inc., Boston, MA (US); Beth Israel Deaconess Medical Center, Boston, MA (US)

(72) Inventors: David Avigan, Sharon, MA (US); Jacalyn Rosenblatt, Newton, MA (US); Donald Kufe, Wellesley, MA (US)

(73) Assignees: Dana-Farber Cancer Institute, Inc., Boston, MA (US); Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 15/563,199

(22) PCT Filed: Mar. 30, 2016

(86) PCT No.: PCT/US2016/024986
§ 371 (c)(1),
(2) Date: Sep. 29, 2017

(87) PCT Pub. No.: WO2016/160973
PCT Pub. Date: Oct. 6, 2016

(65) Prior Publication Data
US 2018/0085350 A1      Mar. 29, 2018

Related U.S. Application Data

(60) Provisional application No. 62/140,335, filed on Mar. 30, 2015.

(51) Int. Cl.
| | | |
|---|---|---|
| *A61K 31/4035* | (2006.01) | |
| *A61K 45/06* | (2006.01) | |
| *A61K 31/454* | (2006.01) | |
| *A61K 35/15* | (2015.01) | |
| *C12N 5/12* | (2006.01) | |
| *C12N 5/0784* | (2010.01) | |
| *C12N 5/09* | (2010.01) | |
| *A61K 31/09* | (2006.01) | |

(52) U.S. Cl.
CPC .......... *A61K 31/4035* (2013.01); *A61K 31/09* (2013.01); *A61K 31/454* (2013.01); *A61K 35/15* (2013.01); *A61K 45/06* (2013.01); *C12N 5/0639* (2013.01); *C12N 5/0693* (2013.01); *C12N 5/12* (2013.01); *A61K 2300/00* (2013.01)

(58) Field of Classification Search
CPC ...... C12N 5/12; C12N 5/0693; C12N 5/0639; C12N 5/16; C12N 5/0694; A61K 35/15; A61K 35/13
See application file for complete search history.

(56) References Cited

U.S. PATENT DOCUMENTS

| | | | | |
|---|---|---|---|---|
| 6,653,848 B2 | 11/2003 | Adamian et al. | | |
| 2010/0158909 A1* | 6/2010 | McDonagh | ........ | A61K 51/1027 424/134.1 |
| 2010/0278873 A1* | 11/2010 | Avigan | ............... | A61K 39/0011 424/277.1 |

FOREIGN PATENT DOCUMENTS

| | | |
|---|---|---|
| WO | WO 95/00655 | 1/1995 |
| WO | WO 95/11984 | 5/1995 |
| WO | WO 95/27071 | 10/1995 |

OTHER PUBLICATIONS

Sasikumar and Ramachandra (BioDrugs, 2018, 17 pages) (Year: 2018).*
NCT01067287 (Archive of ClinicalTrial.Gov, Nov. 22, 2013) (Year: 2013).*
Pardoll (Nature Reviews Cancer, 2012, vol. pp. 252-263) (Year: 2012).*
Abstract of Greene et al (Annals of Surgical Oncology, Feb. 2015, vol. 22, No. 1, suppl. 1, p. S23, abstract No. 51) (Year: 2015).*
NCT00622401 (Archives for ClinicalTrials.Gov, Nov. 22, 2013) (Year: 2013).*
Luptakova et al (Cancer Immunol. Immunother., 2013, vol. 62, pp. 39-49) (Year: 2013).*
Avigan et al (Clinical Cancer Research, 2004, Vo. 10, pp. 4699-4708 (Year: 2004).*
Allavena P. et al. "IL-10 prevents the differentiation of monocytes to dendritic cells but promotes their maturation to macrophages", Eur. J. Immunol., 1998, vol. 28, p. 359-369.
Allen M. et al. "A Comprehensive Polymerase Chain Reaction-Oligonucleotide Typing System for the HLA Class I A Locus", Human Immunology, 1994, vol. 40, p. 25-32.
Amato R. "Vaccine Therapy for Renal Cell Carcinoma", Reviews in Urology, vol. 5, No. 2, 2003, p. 65-71.
Asavaroengchai W. et al., "Tumor lysate-pulsed dendritic cells can elicit an effective antitumor immune response during early lymphoid recovery", Proc Natl Acad Sci USA, 2002, vol. 99, p. 931-936.
Ashley D. et al. "Bone Marrow—generated Dendritic Cells Pulsed with Tumor Extracts or Tumor RNA Induce Antitumor Immunity against Central Nervous System Tumors", J Exp Med, 1997, vol. 186, p. 1177-1182.
Avigan D. "Dendritic cells: development, function and potential use for cancer immunotherapy", Blood Reviews, 1999, vol. 13, p. 51-64.
Banchereau J. et al. "Dendritic cells and the control of immunity", Nature, 1998, vol. 392, p. 245-252.
Bender A. et al. "Improved methods for the generation of dendritic cells from nonproliferating progenitors in human blood", J. Immun. Meth. 1996, vol. 196, p. 121-135.

(Continued)

*Primary Examiner* — Karen A. Canella
(74) *Attorney, Agent, or Firm* — Foley Hoag LLP

(57) ABSTRACT

The present invention provides compositions and methods for treating cancer.

16 Claims, No Drawings

(56) References Cited

OTHER PUBLICATIONS

Dhodapkar M. et al. "Antigen-specific Inhibition of Effector T Cell Function in Humans after Injection of Immature Dendritic Cells", J Exp Med. 2001, vol. 193, No. 2, p. 233-238.

Freeman G. et al. "Cloning of B7-2: A CTLA-4 Counter-Receptor That Costimulates Human T Cell Proliferation", Science 1993, vol. 262, p. 909-911.

Freudenthal P. et al. "The distinct surface of human blood dendritic cells, as observed after an improved isolation method", Proc. Natl Acad Sci USA, 1990, vol. 87, p. 7698-7702.

Gabrilovich D. et al. "Decreased Antigen Presentation by Dendritic Cells in Patients with Breast Cancer", Clinical Cancer Research, 1997, vol. 3, p. 483-490.

Gabrilovich D. et al. "Vascular Endothelial Growth Factor Inhibits the Development of Dendritic Cells and Dramatically Affects the Differentiation of Multiple Hematopoietic Lineages In Vivo", Blood, 1998, vol. 92, p. 4150-4166.

Gabrilovich D. "Mechanisms and Functionla Significance of Tumour-Induced Dendritic-Cell Defects", Nature Reviews/ Immunology, 2004, vol. 4, p. 941-952.

Hermonat and Muzyczka "Use of adeno-associated virus as a mammalian DNA cloning vector: Transduction of neomycin resistance into mammalian tissue culture cells", PNAS USA, 1984, vol. 81, p. 6466-6470.

Hurley C.K. et al. "The search for HLA-matched donors: a summary of HLA-A*, -B*, -DRB1/3/4/5* alleles and their association with serologically defined HLA-A, -B, -DR antigens", Tissue Antigens, 1997, vol. 50, p. 401-415.

Inaba K. et al. "Identification of Proliferating Dendritic Cell Precursors in Mouse Blood", J. Exp. Med, 1992, vol. 175, p. 1157-1167.

Inaba K. et al. "Generation of Large Numbers of Dendritic Cells from Mouse Bone Marrow Cultures Supplemented with Granulocyte/Macrophage Colony-stimulating Factor", J. Exp Med, 1992, vol. 176, p. 1693-1702.

Lebkowski et al. "Adeno-Associated Virus: a Vector System for Efficient Introduction and Integration of DNA into a Variety of Mammalian Cell Types", Molecular and Cellular Biology, 1988, vol. 8, No. 10, p. 3988-3996.

Nabavi N. et al. "Signalling through the MHC class II cytoplasmic domain is required for antigen presentation and induces B7 expression", Nature, 1992, vol. 360, p. 266-268.

Pyzer A. et al. "Clinical trials of dendritic cell-based cancer vaccines in hematologic malignancies", Human Vaccines & Immunotherapeutics, 2014, vol. 10, No. 11, p. 3125-3131.

Romani N. et al. Cultured Human Langerhans Cells Resemble Lymphoid Dendritic Cells in Phenotype and Function, J. Invest. Dermatol, 1989, vol. 93, No. 5, p. 600-609.

Romani N. et al. "Proliferating Dendritic Cell Progenitors in Human Blood", J. Exp. Med., 1994, vol. 180, p. 83-93.

Romani N. et al. "Generation of mature dendritic cells from human blood. An improved method with special regard to clinical applicability", Journal of Immunological Methods, 1996, vol. 196, p. 137-151.

Rosenblatt J. et al. "Vaccination with Dendritic Cell/Tumor Fusions following Autologous Stem Cell Transplant Induces Immunologic and Clinical Responses in Multiple Myeloma Patients", Clinical Cancer Research, vol. 19, No. 13, 2013, p. 3640-3648. XP55280013.

Sallusto F. et al. "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor $\alpha$", J. Exp. Med, 1994, vol. 179, p. 1109-1118.

Santamaria P. et al. "HLA Class I Sequence-Based Typing", Human Immunology, 1993, vol. 37, p. 39-50.

Schuler G. et al. "Murine Epidermal Langerhans Cells Mature Into Potent Immunostimulatory Dendritic Cells in vitro", J. Exp. Med, 1985, vol. 161, p. 526-546.

Steinman R. et al. "Identification of a Novel Cell Type in Peripheral Lymphoid Organs of Mice", J. Exp. Med, 1979, vol. 149, p. 1-16.

Young J. et al. "The B7/BB1 Antigen Provides One of Several Costimulatory Signals for the Activation of CD4+ T Lymphocytes by Human Blood Dendritic Cells In Vitro", J. Clin. Invest, 1992, vol. 90, p. 229-237.

International Preliminary Report on Patentability for International Application No. PCT/US16/24986 dated Oct. 3, 2017.

International Search Report Written Opinion for International Application No. PCT/US16/24986 dated Jul. 7, 2016.

Rosenblatt et al., "CT-011, anti-PD-1 antibody, enhances ex-vivo T cell responses to autologous dendritic/myeloma fusion vaccine developed for the treatment of multiple myeloma," Blood, 114:781 (2009).

Rosenblatt et al., "Clinical trial evaluating DC/AML fusion cell vaccination in AML patients," Blood, 122:3928 (2013).

* cited by examiner

COMPOSITIONS AND METHODS OF TREATING CANCER

RELATED APPLICATIONS

This application is a national stage entry of PCT Application No. PCT/US2016/024986, filed on Mar. 30, 2016, which claims priority to, and the benefit of, U.S. Provisional Application No. 62/140,335, filed on Mar. 30, 2015, the contents of which are hereby incorporated herein by reference in their entirety.

GOVERNMENT INTEREST

This invention was made with government support under grant number CA100707 awarded by The National Institutes of Health. The government has certain rights in the invention

FIELD OF THE INVENTION

The present invention relates generally to cellular immunology and more particularly to and methods for treating cancer by administering dendritic cell/tumor fusions in combination with an immunomodulatory agents.

BACKGROUND OF THE INVENTION

Lenalidomide has been used to successfully treat both inflammatory disorders and cancers in the past 10 years. There are multiple mechanisms of action, and they can be simplified by organizing them as mechanisms of action in vitro and in vivo. In vitro, lenalidomide has three main activities: direct anti-tumor effect, inhibition of angiogenesis, and immunomodulatory role. In vivo, lenalidomide induces tumor cell apoptosis directly and indirectly by inhibition of bone marrow stromal cell support, by anti-angiogenic and anti-osteoclastogenic effects, and by immunomodulatory activity. Lenalidomide and its derivatives have a broad range of activities that can be exploited to treat many hematologic and solid cancers.

SUMMARY OF THE INVENTION

The invention features methods of treating a tumor in a patient by administering to said patient a composition containing a population of autologous dendritic cell/tumor cell fusions (DC/tumor fusions) and an immunomodulatory agent. The immunomodulatory agent is lenalidomide pomalinomide, or apremilast. The composition contains about $1 \times 10^6$ to $1 \times 10^7$ DC/tumor fusions.

The tumor is a solid tumor such as a breast tumor, or a renal tumor. Alternatively the tumor is a hematologic malignancy such as acute myeloid leukemia (AML) or multiple myeloma (MM).

In various aspects the method further includes administering a checkpoint inhibitor. The checkpoint inhibitor is administered one week after the DC/tumor fusions. The patient receives a total of three doses of the checkpoint inhibitor. The checkpoint inhibitor is a PD1, PDL1, PDL2, TIM3, LAG3 inhibitor. Preferably, the checkpoint inhibitor is a PD1, PDL1, TIM3, LAG3 antibody.

In other aspects, the method further includes administering to the subject an agent that target regulatory T cells In a further aspect, the method further includes administering to the subject an immunomodulatory agent. The immunomodulatory agent is lenalidomide or pomalinomide or apremilast.

In yet another aspect, he method further includes administering to the subject a TLR agonist, CPG ODN, polyIC, or tetanus toxoid.

In some embodiments, the tumor is multiple myeloma and the patient has received an autologous stem cell transplant 30 to 100 days prior to the administration of the DC/tumor fusions. In other embodiments the tumor is AML and the patient is in post chemotherapy induced remission or with active disease.

In some embodiments, the composition is administered 4 to 12 weeks following the completion of chemotherapy. In other embodiments the composition is administered following surgical resection of tumor for metastatic disease or as adjuvant therapy after removal of the primary tumor.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

The invention features immune system-stimulating compositions that contain cells formed by fusion between autologous dendritic cells (DCs) and tumor cells (TCs) and there use in a co-therapy with an immunomodulatory agents.

Immunomodulatory drugs (IMiDs) are a class of drugs that constitute thalidomide and its analogues, lenalidomide, pomalidomide and apremilast.

IMiDs inhibit the production of tumour necrosis factor, interleukin 6 and immunoglobulin G and VEGF (which leads to its anti-angiogenic effects), co-stimulates T cells and NK cells and increases interferon gamma and interleukin 2 production. Thus the combination of IMiDs with specific immunotherapy using the DC/TC fusion vaccines will further expand tumor specific T cells.

According in one aspect the invention provides cell fusion of autologous DCs and tumor cell cells obtained from a subject that having cancer. More specifically, the invention provides are methods of treating cancer by administering to a patient the autologous cell fusions according to the invention. The tumor or cancer cells contemplated for use in connection with the invention include, but are not limited to, breast cancer cells, ovarian cancer cells, pancreatic cancer cells, prostate gland cancer cells, renal cancer cells, lung cancer cells, urothelial cancer cells, colon cancer cells, rectal cancer cells, or hematological cancer cells. For example, hematological cancer cells include, but are not limited to, acute myeloid leukemia cells, acute lymphoid leukemia cells, multiple myeloma cells, and non-Hodgkin's lymphoma cells. Moreover, those skilled in the art would recognize that any tumor or cancer cell may be used in any of the methods of the present invention.

In some aspects the patient has undergone therapy for the cancer. In other aspects the patient is in post chemotherapy induced remission. In another aspect the patient has had surgery to remove all or part of the tumor. For example, if the patient has multiple myeloma the patient may have an autologous stem cell transplant 30 to 100 days prior to the administration of the DC/tumor fusions. If the patient has renal cell carcinoma, the patient may have a de-bulking nephrectomy prior to the administration of the DC/tumor fusions DCs can be obtained from bone marrow cultures, peripheral blood, spleen, or any other appropriate tissue of a mammal using protocols known in the art. Bone marrow contains DC progenitors, which, upon treatment with cytokines, such as granulocyte-macrophage colony-stimulating factor ("GM-CSF") and interleukin 4 ("IL-4"), proliferate and differentiate into DCs. Tumor necrosis cell factor (TNF) is optionally used alone or in conjunction with GM-CSF and/or IL-4 to promote maturation of DCs. DCs obtained from bone marrow are relatively immature (as compared to, for instance, spleen DCs). GM-CSF/IL-4 stimulated DC express MHC class I and class II molecules, B7-1, B7-2, ICAM, CD40 and variable levels of CD83. These immature DCs are more amenable to fusion (or antigen uptake) than the more mature DCs found in spleen, whereas more mature DCs are relatively more effective antigen presenting cells. Peripheral blood also contains relatively immature DCs or DC progenitors, which can propagate and differentiate in the presence of appropriate cytokines such as GM-CSF and-which can also be used in fusion.

Preferably, the DCs are obtained from peripheral blood. For example, the DCs are obtained from the patient's peripheral blood after it has been documented that the patient is in complete remission.

The DCs must have sufficient viability prior to fusion. The viability of the DCs is at least 70%, at least 75%, at least 80% or greater.

Prior to fusion the population of the DCs are free of components used during the production, e.g., cell culture components and substantially free of mycoplasm, endotoxin, and microbial contamination. Preferably, the population of DCs has less than 10, 5, 3, 2, or 1 CFU/swab. Most preferably the population of DCs has 0 CFU/swab.

The tumor cells must have sufficient viability prior to fusion. The viability of the tumor cells is at least 50%, at least 60%, at least 70%, at least 80% or greater.

Prior to fusion the population of tumor cells are free of components used during the production, e.g., cell culture components and substantially free of mycoplasm, endotoxin, and microbial contamination. Preferably, the population of tumor cell population has less than 10, 5, 3, 2, or 1 CFU/swab. Most preferably the population of tumor cells has 0 CFU/swab. The endotoxin level in the population of tumor cells is less than 20 EU/mL, less than 10 EU/mL or less than 5 EU/mL.

The fusion product is used directly after the fusion process (e.g., in antigen discovery screening methods or in therapeutic methods) or after a short culture period.

Fused cells are irradiated prior to clinical use. Irradiation induces expression of cytokines, which promote immune effector cell activity.

In the event that the fused cells lose certain DC characteristics such as expression of the APC-specific T-cell stimulating molecules, primary fused cells can be refused with dendritic cells to restore the DC phenotype. The refused cells (i.e., secondary fused cells) are found to be highly potent APCs. The fused cells can be refused with the dendritic or non-dendritic parental cells as many times as desired.

Fused cells that express MHC class II molecules, B7, or other desired T-cell stimulating molecules can also be selected by panning or fluorescence-activated cell sorting with antibodies against these molecules.

Fusion between the DCs and the tumor cells can be carried out with well-known methods such as those using polyethylene glycol ("PEG"), Sendai virus, or electrofusion. DCs are autologous or allogeneic. (See, e.g., U.S. Pat. No. 6,653,848, which is herein incorporated by reference in its entirety). The ratio of DCs to tumor cells in fusion can vary from 1:100 to 1000:1, with a ratio higher than 1:1 being preferred. Preferably, the ratio is 1:1, 5:1, or 10:1. Most preferably, the ratio of DCs to tumor cells is 10:1 or 3:1. After fusion, unfused DCs usually die off in a few days in culture, and the fused cells can be separated from the unfused parental non-dendritic cells by the following two methods, both of which yield fused cells of approximately 50% or higher purity, i.e., the fused cell preparations contain less than 50%, and often less than 30%, unfused cells.

Specifically, one method of separating unfused cells from fused cells is based on the different adherence properties between the fused cells and the non-dendritic parental cells. It has been found that the fused cells are generally lightly adherent to tissue culture containers. Thus, if the non-dendritic parental cells are much more adherent, e.g., in the case of carcinoma cells, the post-fusion cell mixtures can be cultured in an appropriate medium for a short period of time (e.g., 5-10 days). Subsequently, the fused cells can be gently dislodged and aspirated off, while the unfused cells grow firmly attached to the tissue culture containers. Conversely, if the tumor cells grow in suspension, after the culture period, they can be gently aspirated off while leaving the fused cells loosely attached to the containers. Alternatively, the hybrids are used directly without an in vitro cell culturing step.

Fused cells obtained by the above-described methods typically retain the phenotypic characteristics of DCs. For instance, these fused cells express T-cell stimulating molecules such as MHC class II protein, B7-1, B7-2, and adhesion molecules characteristic of APCs such as ICAM-1. The fused cells also continue to express cell-surface antigens of the tumor cells such as MUC-1, and are therefore useful for inducing immunity against the cell-surface antigens.

In the event that the fused cells lose certain DC characteristics such as expression of the APC-specific T-cell stimulating molecules, they (i.e., primary fused cells) can be re-fused with dendritic cells to restore the DC phenotype. The re-fused cells (i.e., secondary fused cells) are found to be highly potent APCs, and in some cases, have even less tumorigenicity than primary fused cells. The fused cells can be re-fused with the dendritic or non-dendritic parental cells as many times as desired.

The fused cells may be frozen before administration. The fused cells are frozen in a solution containing 10% DMSO in 90% autologous heat inactivated autologous plasma.

The fused cells of the invention can be used to stimulate the immune system of a mammal for treatment or prophylaxis of cancer. For instance, to treat cancer in a human, a composition containing fused cells formed by his own DCs and tumor cells can be administered to him, e.g., at a site near the lymphoid tissue. Preferably, the vaccine is administered to four different sites near lymphoid tissue. The composition may be given multiple times (e.g., two to five, preferably three) at an appropriate intervals, preferably, four weeks and dosage (e.g., approximately $10^5$-$10^8$, e.g., about $0.5 \times 10^6$ to $1 \times 10^6$, fused cells per administration). Preferably each dosage contains approximately $1 \times 10^6$ to $1 \times 10^7$ fused cells. More preferably each dosage contains approximately $5 \times 10^6$ fused cells. In addition the fused cells the patient further receives GM-CSF. The GM-CSF is administered on the day the fused cells are administered and for daily for three subsequent days. The GM-CSF is administered subcutaneously at a dose of 100 µg. The GM-CSF is administered at the site where the fused cells are administered.

The patient further receives an immunomodulatory drug such as thalidomide lenalidomide, pomalidomide or apremilast. The immunomodulatory drug is administered at a therapeutic dose. For example, the patient receives 5 mg, 10 mg, 15 mg, 20 mg, 25 mg or more per day. In other aspects, the immunomodulatory drug is administered at a sub-therapeutic dose. By sub-therapeutic dose it is meant below the level typically necessary to treat disease.

Optionally, the patient further receives a checkpoint inhibitor. The check point inhibitor is administered contemporaneously with the fused cell, prior to administration of the fused cells or after administration of the fused cells. For example, the checkpoint inhibitor is administered 1 week prior to the fused cells. Preferably, the checkpoint inhibitor is administered 1 week after the fused cells. The checkpoint inhibitor is administered at 1, 2, 3, 4, 5, 6 week intervals.

By checkpoint inhibitor it is meant that at the compound inhibits a protein in the checkpoint signally pathway. Proteins in the checkpoint signally pathway include for example, PD-1, PD-L1, PD-L2, TIM3, LAG3, and CTLA-4. Checkpoint inhibitors are known in the art. For example, the checkpoint inhibitor can be a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than 300 daltons, less than 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules.

Alternatively the checkpoint inhibitor is an antibody is an antibody or fragment thereof. For example, the antibody or fragment thereof is specific to a protein in the checkpoint signaling pathway, such as PD-1, PD-L1, PD-L2, TIM3, LAG3, or CTLA-4. Preferably, the checkpoint inhibitor is an antibody specific for PD-1, PD-L1, PD-L2, TIM3, LAG3, or CTLA-4.

To monitor the effect of vaccination, cytotoxic T lymphocytes obtained from the treated individual can be tested for their potency against cancer cells in cytotoxic assays. Multiple boosts may be needed to enhance the potency of the cytotoxic T lymphocytes.

Compositions containing the appropriate fused cells are administered to an individual (e.g., a human) in a regimen determined as appropriate by a person skilled in the art. For example, the composition may be given multiple times (e.g., three to five times, preferably three) at an appropriate interval (e.g., every four weeks) and dosage (e.g., approximately $10^5$-$10^8$, preferably about $1 \times 10^6$ to $1 \times 10^7$, more preferably $5 \times 10^6$ fused cells per administration).

The composition of fused cells prior to administration to the patient must have sufficient viability. The viability of the fused cells at the time of administration is at least 50%, at least 60%, at least 70%, at least 80% or greater.

Prior to administration, the population of fused cells are free of components used during the production, e.g., cell culture components and substantially free of mycoplasm, endotoxin, and microbial contamination. Preferably, the population of fused cells has less than 10, 5, 3, 2, or 1 CFU/swab. Most preferably the population of tumor cells has 0 CFU/swab. For example, the results of the sterility testing is "negative" or "no growth". The endotoxin level in the population of tumor cells is less than 20 EU/mL, less than 10 EU/mL or less than 5 EU/mL. The results of the myoplasm testing is "negative".

Prior to administration, the fused cell must express at least 40%, at least 50%, at least 60% CD86 as determined by immunological staining. Preferably the fused cells express at least 50% CD86.

More specifically, all final cell product must conform with rigid requirements imposed by the Federal Drug Administration (FDA). The FDA requires that all final cell products must minimize "extraneous" proteins known to be capable of producing allergenic effects in human subjects as well as minimize contamination risks. Moreover, the FDA expects a minimum cell viability of 70%, and any process should consistently exceed this minimum requirement.

Definitions

The practice of the present invention employs, unless otherwise indicated, conventional techniques of molecular biology, microbiology, cell biology and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel et al. eds., (1987)); the series METHODS IN ENZYMOLOGY (Academic Press, Inc.): PCR 2: A PRACTICAL APPROACH (Mi. MacPherson, B. D. Hames and G. R. Taylor eds. (1995)) and ANIMAL CELL CULTURE (Rd. Freshney, ed. (1987)).

As used herein, certain terms have the following defined meanings. As used in the specification and claims, the singular form "a", "an" and "the" include plural references unless the context clearly dictates otherwise. For example, the term "a cell" includes a plurality of cells, including mixtures thereof.

The term "immune effector cells" refers to cells that specifically recognize an antigen present, for example on a neoplastic or tumor cell. For the purposes of this invention, immune effector cells include, but are not limited to, B cells; monocytes; macrophages; NK cells; and T cells such as cytotoxic T lymphocytes (CTLs), for example CTL lines, CTL clones, and CTLs from tumor, inflammatory sites or other infiltrates. "T-lymphocytes" denotes lymphocytes that are phenotypically CD3+, typically detected using an anti-CD3 monoclonal antibody in combination with a suitable labeling technique. The T-lymphocytes of this invention are also generally positive for CD4, CD8, or both. The term "naïve" immune effector cells refers to immune effector cells that have not encountered antigen and is intended to by synonymous with unprimed and virgin. "Educated" refers to immune effector cells that have interacted with an antigen such that they differentiate into an antigen-specific cell.

The terms "antigen presenting cells" or "APCs" includes both intact, whole cells as well as other molecules which are capable of inducing the presentation of one or more antigens, preferably with class I MHC molecules. Examples of suitable APCs are discussed in detail below and include, but are not limited to, whole cells such as macrophages, dendritic cells, B cells; purified MHC class I molecules complexed to β2-microglobulin; and foster antigen presenting cells.

Dendritic cells (DCs) are potent APCs. DCs are minor constituents of various immune organs such as spleen, thymus, lymph node, epidermis, and peripheral blood. For instance, DCs represent merely about 1% of crude spleen (see Steinman et al. (1979) J. Exp. Med 149: 1) or epidermal cell suspensions (see Schuler et al. (1985) J. Exp. Med 161:526; Romani et al. J. Invest. Dermatol (1989) 93: 600) and 0.1-1% of mononuclear cells in peripheral blood (see Freudenthal et al. Proc. Natl Acad Sci USA (1990) 87: 7698). Methods for isolating DCs from peripheral blood or bone marrow progenitors are known in the art. (See Inaba et al. (1992) J. Exp. Med 175:1157; Inaba et al. (1992) J. Exp, Med 176: 1693-1702; Romani et al. (1994) J. Exp. Med. 180: 83-93; Sallusto et al. (1994) J. Exp. Med 179: 1109-1118)). Preferred methods for isolation and culturing of DCs are described in Bender et al. (1996) J. Immun. Meth. 196:121-135 and Romani et al. (1996) J. Immun. Meth 196:137-151.

Dendritic cells (DCs) represent a complex network of antigen presenting cells that are primarily responsible for initiation of primary immunity and the modulation of immune response. (See Avigan, Blood Rev. 13:51-64 (1999); Banchereau et al., Nature 392:245-52 (1998)). Partially mature DCs are located at sites of antigen capture, excel at the internalization and processing of exogenous antigens but are poor stimulators of T cell responses. Presentation of antigen by immature DCs may induce T cell tolerance. (See Dhodapkar et al., J Exp Med. 193:233-38 (2001)). Upon activation, DCs undergo maturation characterized by the increased expression of costimulatory molecules and CCR7, the chemokine receptor which promotes migration to sites of T cell traffic in the draining lymph nodes. Tumor or cancer cells inhibit DC development through the secretion of IL-10, TGF-β, and VEGF resulting in the accumulation of immature DCs in the tumor bed that potentially suppress anti-tumor responses. (See Allavena et al., Eur. J. Immunol. 28:359-69 (1998); Gabrilovich et al., Clin Cancer Res. 3:483-90 (1997); Gabrilovich et al., Blood 92:4150-66 (1998); Gabrilovich, Nat Rev Immunol 4:941-52 (2004)). Conversely, activated DCs can be generated by cytokine mediated differentiation of DC progenitors ex vivo. DC maturation and function can be further enhanced by exposure to the toll like receptor 9 agonist, CPG ODN. Moreover, DCs can be manipulated to present tumor antigens potently stimulate anti-tumor immunity. (See Asavaroenhchai et al., Proc Natl Acad Sci USA 99:931-36 (2002); Ashley et al., J Exp Med 186:1177-82 (1997)).

"Foster antigen presenting cells" refers to any modified or naturally occurring cells (wild-type or mutant) with antigen presenting capability that are utilized in lieu of antigen presenting cells ("APC") that normally contact the immune effector cells they are to react with. In other words, they are any functional APCs that T cells would not normally encounter in vivo.

It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC") class I or II protein on the surface of APCs. This interaction is necessary, but not sufficient, for T cell activation to occur. In fact, without the second type of signals, the first type of signals can result in T cell anergy. The second type of signals, called costimulatory signals, are neither antigen-specific nor MHC restricted, and can lead to a full proliferation response of T cells and induction of T cell effector functions in the presence of the first type of signals.

Thus, the term "cytokine" refers to any of the numerous factors that exert a variety of effects on cells, for example, inducing growth or proliferation. Non-limiting examples of cytokines include, IL-2, stem cell factor (SCF), IL-3, IL-6, IL-7, IL-12, IL-15, G-CSF, GM-CSF, IL-1 α, IL-1 β, MIP-1 α, LIF, c-kit ligand, TPO, and flt3 ligand. Cytokines are commercially available from several vendors such as, for example, Genzyme Corp. (Framingham, Mass.), Genentech (South San Francisco, Calif.), Amgen (Thousand Oaks, Calif.) and Immunex (Seattle, Wash.). It is intended, although not always explicitly stated, that molecules having similar biological activity as wild-type or purified cytokines (e.g., recombinantly produced cytokines) are intended to be used within the spirit and scope of the invention and therefore are substitutes for wild-type or purified cytokines.

"Costimulatory molecules" are involved in the interaction between receptor-ligand pairs expressed on the surface of antigen presenting cells and T cells. One exemplary receptor-ligand pair is the B7 co-stimulatory molecules on the surface of DCs and its counter-receptor CD28 or CTLA-4 on T cells. (See Freeman et al. (1993) Science 262:909-911; Young et al. (1992) J. Clin. Invest 90: 229; Nabavi et al. Nature 360:266)). Other important costimulatory molecules include, for example, CD40, CD54, CD80, and CD86. These are commercially available from vendors identified above.

A "hybrid" cell refers to a cell having both antigen presenting capability and also expresses one or more specific antigens. In one embodiment, these hybrid cells are formed by fusing, in vitro, APCs with cells that are known to express the one or more antigens of interest. As used herein, the term "hybrid" cell and "fusion" cell are used interchangeably.

A "control" cell refers to a cell that does not express the same antigens as the population of antigen-expressing cells.

The term "culturing" refers to the in vitro propagation of cells or organisms on or in media of various kinds, it is understood that the descendants 30 of a cell grown in culture may not be completely identical (i.e., morphologically, genetically, or phenotypically) to the parent cell. By "expanded" is meant any proliferation or division of cells.

An "effective amount" is an amount sufficient to effect beneficial or desired results. An effective amount can be administered in one or more administrations, applications or dosages. For purposes of this invention, an effective amount of hybrid cells is that amount which promotes expansion of the antigenic-specific immune effector cells, e.g., T cells.

An "isolated" population of cells is "substantially free" of cells and materials with which it is associated in nature. By "substantially free" or "substantially pure" is meant at least 50% of the population are the desired cell type, preferably at least 70%, more preferably at least 80%, and even more preferably at least 90%. An "enriched" population of cells is at least 5% fused cells. Preferably, the enriched population contains at least 10%, more preferably at least 20%, and most preferably at least 25% fused cells.

The term "autogeneic", or "autologous", as used herein, indicates the origin of a cell. Thus, a cell being administered to an individual (the "recipient") is autogeneic if the cell was derived from that individual (the "donor") or a genetically identical individual (i.e., an identical twin of the individual). An autogeneic cell can also be a progeny of an autogeneic cell. The term also indicates that cells of different cell types are derived from the same donor or genetically identical donors. Thus, an effector cell and an antigen presenting cell are said to be autogeneic if they were derived from the same donor or from an individual genetically identical to the donor, or if they are progeny of cells derived from the same donor or from an individual genetically identical to the donor.

Similarly, the term "allogeneic", as used herein, indicates the origin of a cell. Thus, a cell being administered to an individual (the "recipient") is allogeneic if the cell was derived from an individual not genetically identical to the recipient. In particular, the term relates to non-identity in expressed MHC molecules. An allogeneic cell can also be a progeny of an allogeneic cell. The term also indicates that cells of different cell types are derived from genetically nonidentical donors, or if they are progeny of cells derived from genetically non-identical donors. For example, an APC is said to be allogeneic to an effector cell if they are derived from genetically non-identical donors.

A "subject" is a vertebrate, preferably a mammal, more preferably a human. Mammals include, but are not limited to, murines, simians, humans, farm animals, sport animals, and pets.

As used herein, "genetic modification" refers to any addition, deletion or disruption to a cell's endogenous nucleotides.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors and the like. In aspects where gene transfer is mediated by a retroviral vector, a vector construct refers to the polynucleotide comprising the retroviral genome or part thereof, and a therapeutic gene.

As used herein, the terms "retroviral mediated gene transfer" or "retroviral transduction" carries the same meaning and refers to the process by which a gene or a nucleic acid sequence is stably transferred into the host cell by virtue of the virus entering the cell and integrating its genome into the host cell genome. The virus can enter the host cell via its normal mechanism of infection or be modified such that it binds to a different host cell surface receptor or ligand to enter the cell.

Retroviruses carry their genetic information in the form of RNA. However, once the virus infects a cell, the RNA is reverse-transcribed into the DNA form that integrates into the genomic DNA of the infected cell. The integrated DNA form is called a provirus.

In aspects where gene transfer is mediated by a DNA viral vector, such as a adenovirus (Ad) or adeno-associated virus (AAV), a vector construct refers to the polynucleotide comprising the viral genome or part thereof, and a therapeutic gene. Adenoviruses (Ads) are a relatively well characterized, homogenous group of viruses, including over 50 serotypes. (See, e.g., WO 95/27071). Ads are easy to grow and do not integrate into the host cell genome. Recombinant Ad-derived vectors, particularly those that reduce the potential for recombination and generation of wild-type virus, have also been constructed. (See, WO 95/00655; WO 95/11984). Wild-type AAV has high infectivity and specificity integrating into the host cells genome. (See Hermonat and Muzyczka (1984) PNAS USA 81:6466-6470; Lebkowski et al., (1988) Mol Cell Biol 8:3988-3996).

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of suitable vectors are viruses, such as baculovirus and retrovirus, bacteriophage, cosmid, plasmid, fungal vectors and other recombination vehicles typically used in the art which have been described for expression in a variety of eucaryotie and prokaryotic hosts, and may be used for gene therapy as well as for simple protein expression.

Among these are several non-viral vectors, including DNA/liposome complexes, and targeted viral protein DNA complexes. To enhance delivery to a cell, the nucleic acid or proteins of this invention can be conjugated to antibodies or binding fragments thereof which bind cell surface antigens, e.g., TCR, CD3 or CD4. Liposomes that also comprise a targeting antibody or fragment thereof can be used in the methods of this invention. This invention also provides targeting complexes for use in the methods disclosed herein.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV4O for mRNA stability; SV40 polyoma origins of replication and ColEI for proper episomal replication; versatile multiple cloning sites; and T7 and SP6 RNA promoters for in vitro transcription of sense and antisense RNA. Other means are well known and available in the art.

As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. (1989), supra). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general.

The terms "major histocompatibility complex" or "MHC" refers to a complex of genes encoding cell-surface molecules that are required for antigen presentation to immune effector cells such as T cells and for rapid graft rejection. In humans, the MHC complex is also known as the HLA complex. The proteins encoded by the MHC complex are known as "MHC molecules" and are classified into class I and class II MHC molecules. Class I MHC molecules include membrane heterodimeric proteins made up of an α chain encoded in the MHC associated noncovalently with β2-microglobulin. Class I MHC molecules are expressed by nearly all nucleated cells and have been shown to function in antigen presentation to CD8+ T cells. Class I molecules include HLA-A, -B, and -C in humans. Class II MHC molecules also include membrane heterodimeric proteins consisting of noncovalently associated and J3 chains. Class II MHCs are known to function in CD4+ cells and, in humans, include HLA-DP, -DQ, and DR. The term "MHC restriction" refers to a characteristic of T cells that permits them to recognize antigen only after it is processed and the resulting antigenic peptides are displayed in association with either a class I or class II MHC molecule. Methods of identifying and comparing MHC are well known in the art and are described in Allen M. et al. (1994) Human Imm. 40:25-32; Santamaria P. et al. (1993) Human Imm. 37:39-50; and Hurley C. K. et al. (1997) Tissue Antigens 50:401-415.

The term "sequence motif" refers to a pattern present in a group of 15 molecules (e.g., amino acids or nucleotides). For instance, in one embodiment, the present invention provides for identification of a sequence motif among peptides present in an antigen. In this embodiment, a typical pattern may be identified by characteristic amino acid residues, such as hydrophobic, hydrophilic, basic, acidic, and the like.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc.

As used herein the term "amino acid" refers to either natural and/or 25 unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

As used herein, "solid phase support" is used as an example of a "carrier" and is not limited to a specific type of support. Rather a large number of supports are available and are known to one of ordinary skill in the art. Solid phase supports include silica gels, resins, derivatized plastic films, glass beads, cotton, plastic beads, alumina gels. A suitable solid phase support may be selected on the basis of desired end use and suitability for various synthetic protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from MilligenlBiosearch, California). In a preferred embodiment for peptide synthesis, solid phase support refers to polydimethylacrylamide resin.

The term "aberrantly expressed" refers to polynucleotide sequences in a cell or tissue which are differentially expressed (either over-expressed or under-expressed) when compared to a different cell or tissue whether or not of the same tissue type, i.e., lung tissue versus lung cancer tissue.

"Host cell" or "recipient cell" is intended to include any individual cell or cell culture which can be or have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, animal cells, and mammalian cells, e.g., murine, rat, simian or human.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody and its binding partner or ligand.

A "native antigen" is a polypeptide, protein or a fragment containing an epitope, which induces an immune response in the subject.

The term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eucaryotic cell in which it is produced in nature.

A "composition" is intended to mean a combination of active agent and another compound or composition, inert (for example, a detectable agent, carrier, solid support or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI, 15th Ed. (Mack Publ. Co., Easton (1975)).

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected (measured), after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody). Immune effector cells specific for the antigen can be detected any of a variety of assays known to those skilled in the art, including, but not limited to, FACS, or, in the case of CTLs, $^{51}$CR-release assays, or $^{3}$H-thymidine uptake assays.

By substantially free of endotoxin is meant that there is less endotoxin per dose of cell fusions than is allowed by the FDA for a biologic, which is a total endotoxin of 5 EU/kg body weight per day.

By substantially free for mycoplasma and microbial contamination is meant as negative readings for the generally accepted tests know to those skilled in the art. For example, mycoplasm contamination is determined by subculturing a cell sample in broth medium and distributed over agar plates on day 1, 3, 7, and 14 at 37° C. with appropriate positive and negative controls. The product sample appearance is compared microscopically, at 100×, to that of the positive and negative control. Additionally, inoculation of an indicator cell culture is incubated for 3 and 5 days and examined at 600× for the presence of mycoplasmas by epifluorescence microscopy using a DNA-binding fluorochrome. The product is considered satisfactory if the agar and/or the broth media procedure and the indicator cell culture procedure show no evidence of mycoplasma contamination.

The sterility test to establish that the product is free of microbial contamination is based on the U.S. Pharmacopedia Direct Transfer Method. This procedure requires that a pre-harvest medium effluent and a pre-concentrated sample be inoculated into a tube containing tryptic soy broth media and fluid thioglycollate media. These tubes are observed periodically for a cloudy appearance (turbidity) for a 14 day incubation. A cloudy appearance on any day in either medium indicate contamination, with a clear appearance (no growth) testing substantially free of contamination.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of treating a tumor in a patient comprising administering to said patient a composition comprising a population of autologous dendritic cell/tumor cell fusions (DC/tumor fusions) and an immunomodulatory agent, wherein the immunomodulatory agent is pomalidomide and/or apremilast.

2. The method of claim 1, wherein the tumor is a solid tumor.

3. The method of claim 2, wherein said solid tumor is a breast tumor, or a renal tumor.

4. The method of claim 1, wherein the tumor is a hematologic malignancy.

5. The method of claim 4, wherein the hematologic malignancy is acute myeloid leukemia (AML) or multiple myeloma (MM).

6. The method of claim 1, further comprising administering a checkpoint inhibitor.

7. The method of claim 6, wherein the checkpoint inhibitor is administered one week after the DC/tumor fusions.

8. The method of claim 6, wherein the checkpoint inhibitor is a PD1, PDL1, TIM3, or LAG3 antibody.

9. The method of claim 1, wherein the further comprising administering an agent that targets regulatory T cells.

10. The method of claim 1, further comprising administering said subject a TLR agonist or tetanus toxoid.

11. The method of claim 10, wherein the TLR agonist is CPG ODN or polyIC.

12. The method of claim 4, wherein the tumor is multiple myeloma and the patient has received an autologous stem cell transplant 30 to 100 days prior to the administration of the DC/tumor fusions.

13. The method of claim 5, wherein the tumor is AML and the patient is in post chemotherapy induced remission of AML or with active AML disease.

14. The method in claim 2, when the composition is administered following surgical resection of tumor for metastatic disease or as adjuvant therapy after removal of the primary tumor.

15. The method of claim 1, wherein the patient is treated with chemotherapy and the composition is administered 4 to 12 weeks following the completion of the chemotherapy.

16. The method of claim 1, wherein the composition comprises about $1\times10^6$ to $1\times10^7$ DC/tumor fusions.

* * * * *